United States Patent
Liopo et al.

(10) Patent No.: US 9,615,750 B2
(45) Date of Patent: Apr. 11, 2017

(54) METHODS AND COMPOSITIONS FOR CARRIER AGENTS AND CLEARING AGENTS USED IN OPTOACOUSTIC IMAGING SYSTEMS

(75) Inventors: Anton Liopo, Houston, TX (US); Alexander Oraevsky, Houston, TX (US)

(73) Assignee: SENO MEDICAL INSTRUMENTS, INC., San Antonio, TX (US)

( * ) Notice: Subject to any disclaimer, the term of this patent is extended or adjusted under 35 U.S.C. 154(b) by 0 days.

(21) Appl. No.: 13/517,649

(22) Filed: Jun. 14, 2012

(65) Prior Publication Data
US 2013/0338476 A1    Dec. 19, 2013

(51) Int. Cl.
*A61B 5/00* (2006.01)
*A61B 8/08* (2006.01)
*A61B 8/00* (2006.01)

(52) U.S. Cl.
CPC .......... *A61B 5/0095* (2013.01); *A61B 8/0825* (2013.01); *A61B 8/4281* (2013.01); *A61B 2562/146* (2013.01)

(58) Field of Classification Search
CPC ............ A61B 2562/146; A61B 5/0095; A61B 8/0825; A61B 8/4281
USPC ........ 600/407, 443, 476; 606/9; 604/20, 290
See application file for complete search history.

(56) References Cited

U.S. PATENT DOCUMENTS

| 5,971,956 A * | 10/1999 | Epstein ......................... 604/119 |
| 7,740,585 B2 * | 6/2010 | Oraevsky et al. ............ 600/443 |
| 2002/0037269 A1 | 3/2002 | Liotta et al. |

FOREIGN PATENT DOCUMENTS

| JP | 2009137950 | 6/2009 |
| WO | 9606622 | 3/1996 |
| WO | 9930620 | 6/1999 |
| WO | 2011150316 | 12/2011 |

OTHER PUBLICATIONS

Khan, MH et al. "Optical Clearing of In Vivo Human Skin: Implications for Light-Based Diagnostic Imaging and Therapeutics". Lasers in Surgery and Medicine 34:83-85 (2004).*
ISA/KR, International Search Report, Int'l Application No. PCT/US13/45888, Nov. 26, 2013, p. 4.

* cited by examiner

*Primary Examiner* — Michael Rozanski
(74) *Attorney, Agent, or Firm* — Harness, Dickey & Pierce, P.L.C.

(57) ABSTRACT

A method for optoacoustic imaging of a tissue mass after treating the skin overlying a portion of a tissue being imaged to improve optical clarity is presented. In an embodiment, the method involves optoacoustic imaging after first applying a carrier agent such as hyaluronic acid to the skin surface and applying a clearing agent to the skin. A method of temporarily reducing optical scattering (opacity) of skin for diagnostic purposes is also presented. In an embodiment, the method involves applying a liquid comprising at least one of: polyethylene glycol and polypropylene glycol, to the skin, the skin having been pretreated with hyaluronic acid.

16 Claims, 10 Drawing Sheets

METHODS AND COMPOSITIONS FOR CARRIER AGENTS AND CLEARING AGENTS USED IN OPTOACOUSTIC IMAGING SYSTEMS

This application includes material which is subject to copyright protection. The copyright owner has no objection to the facsimile reproduction by anyone of the patent disclosure, as it appears in the Patent and Trademark Office files or records, but otherwise reserves all copyright rights whatsoever.

FIELD

The present invention relates in general to the field of medical imaging, and in particular to the use of clearing agents and carrier agents used in conjunction with optoacoustic imaging equipment.

BRIEF DESCRIPTION OF THE DRAWINGS

The foregoing and other objects, features, and advantages of the invention will be apparent from the following more particular description of preferred embodiments as illustrated in the accompanying drawings, in which reference characters refer to the same parts throughout the various views. The drawings are not necessarily to scale, emphasis instead being placed upon illustrating principles of the invention.

DETAILED DESCRIPTION

Reference will now be made in detail to various embodiments of the present invention, examples of which are illustrated in the accompanying drawings.

The following description and drawings are illustrative and are not to be construed as limiting. Numerous specific details are described to provide a thorough understanding. However, in certain instances, well-known or conventional details are not described in order to avoid obscuring the description. References to one or an embodiment in the present disclosure are not necessarily references to the same embodiment; and, such references mean at least one.

Reference in this specification to "one embodiment" or "an embodiment" means that a particular feature, structure, or characteristic described in connection with the embodiment is included in at least one embodiment of the disclosure. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but no other embodiments.

Optoacoustic Imaging and Clearing Agents

Optoacoustic imaging is an imaging technology based on the optoacoustic effect. When a short laser pulse is used to irradiate tissue there is local absorption of the tissue, causing heating and expansion of the tissue. The expansion of the tissue produces ultrasound that can be recorded, for example, using wide-band ultrasonic transducers (pressure sensors). The slow speed of sound in tissue (e.g., ~1,500 m/s) in comparison to the speed of light allows for the time resolved detection of these pressure waves and determination of a location from where the pressure waves originated. By analyzing information received by an array of sensors during a period following the short laser pulse, an optoacoustic image can be formed.

In various embodiments, an ultrasonic coupling agent is used to improve ultrasound transmission efficiency from skin to the ultrasonic transducers. In an embodiment, the ultrasonic coupling agent can be water, water-based gels, optically transparent oil or oil-based media. Examples include optically clear ultrasonic gels Aquasonic, mineral oil, vegetable oil, etc. Additionally, the ultrasonic coupling agent can include substances that can temporary reduce optical scattering of skin. Alternatively, the substances that reduce optical scattering of skin can be applied to skin prior to application of the ultrasonic coupling agent.

Figure 1:
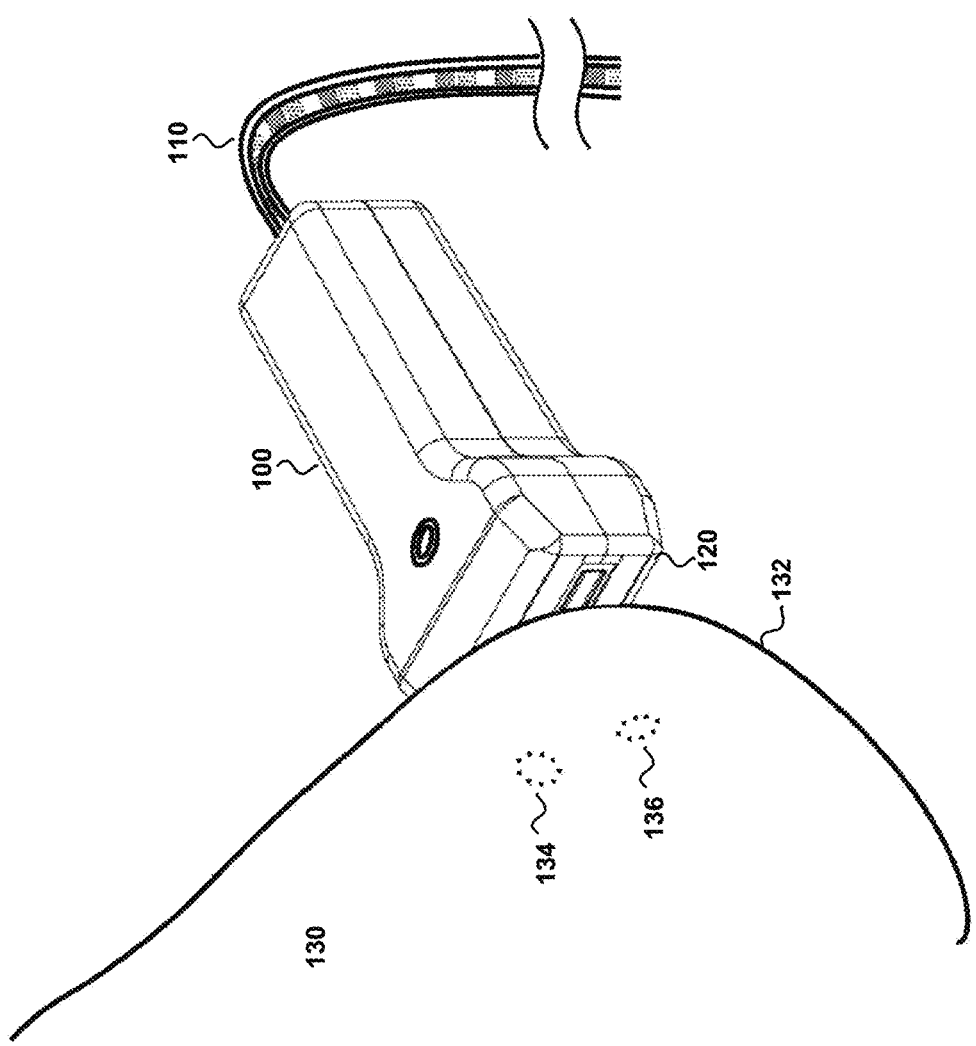
FIG. 1 illustrates an embodiment of a probe that could be used in an optoacoustic imaging system and its use.

FIG. 1 illustrates an embodiment of a probe that could be used in an optoacoustic imaging system and its use.

The probe 100 is connected to an optoacoustic imaging system (not shown) via a cable 110. The cable 110 transmits pulses of laser light to the probe 100 from the optoacoustic imaging system and transmits imaging data from the probe 100 to the optoacoustic imaging system. The head of the probe 120 includes one or more optical windows that project light input to the probe onto adjacent surfaces and one or more arrays of ultrasound transducers that, inter alia, detect ultrasound waves produced in response to light projected by the probe onto adjacent surfaces.

In the illustrated embodiment, the probe is placed adjacent to a tissue mass 130, for example, a breast. The head of the probe 120 projects pulses of laser light onto the skin 132 encasing the tissue mass 130. The pulses of laser light penetrate the skin 132 of the tissue mass 130, at least in part, and are absorbed by various components of the tissue mass such as, for example, tumors 134 and 136. The various tissue components absorb the pulses of laser light and, in response, produce ultrasonic waves that are detected by the transducers in the head 120 of the probe 100. Data relating to such ultrasonic waves are then transmitted, via the cable, to the optoacoustic imaging system for processing As various tissue components such as, for example, the tumors 134 and 136, can produce an optoacoustic response different than surrounding tissue, the ultrasonic data produced in response to the pulses of laser light can be used to create images that provide a representation of tissue components 134 136 in a tissue mass 130.

In various embodiments, optoacoustic imaging can be enhanced through the use of what are referred to as "clearing agents". For the purposes of the present disclosure, the term "clearing agent" should be understood to refer to substances that when applied to skin, render the skin more transparent to light. For example, referring to FIG. 1, in an embodiment, a clearing agent could be applied to the skin 132 surrounding the tissue mass 130. The clearing agent renders the skin 132 more transparent to the light projected, by the head 120 of the probe 110 onto the skin 132. As a result, inter alia, more light penetrates to tissue components 134 and 136, resulting in better optoacoustic data and, ultimately, images providing better resolution of tissue components.

Figure 2:
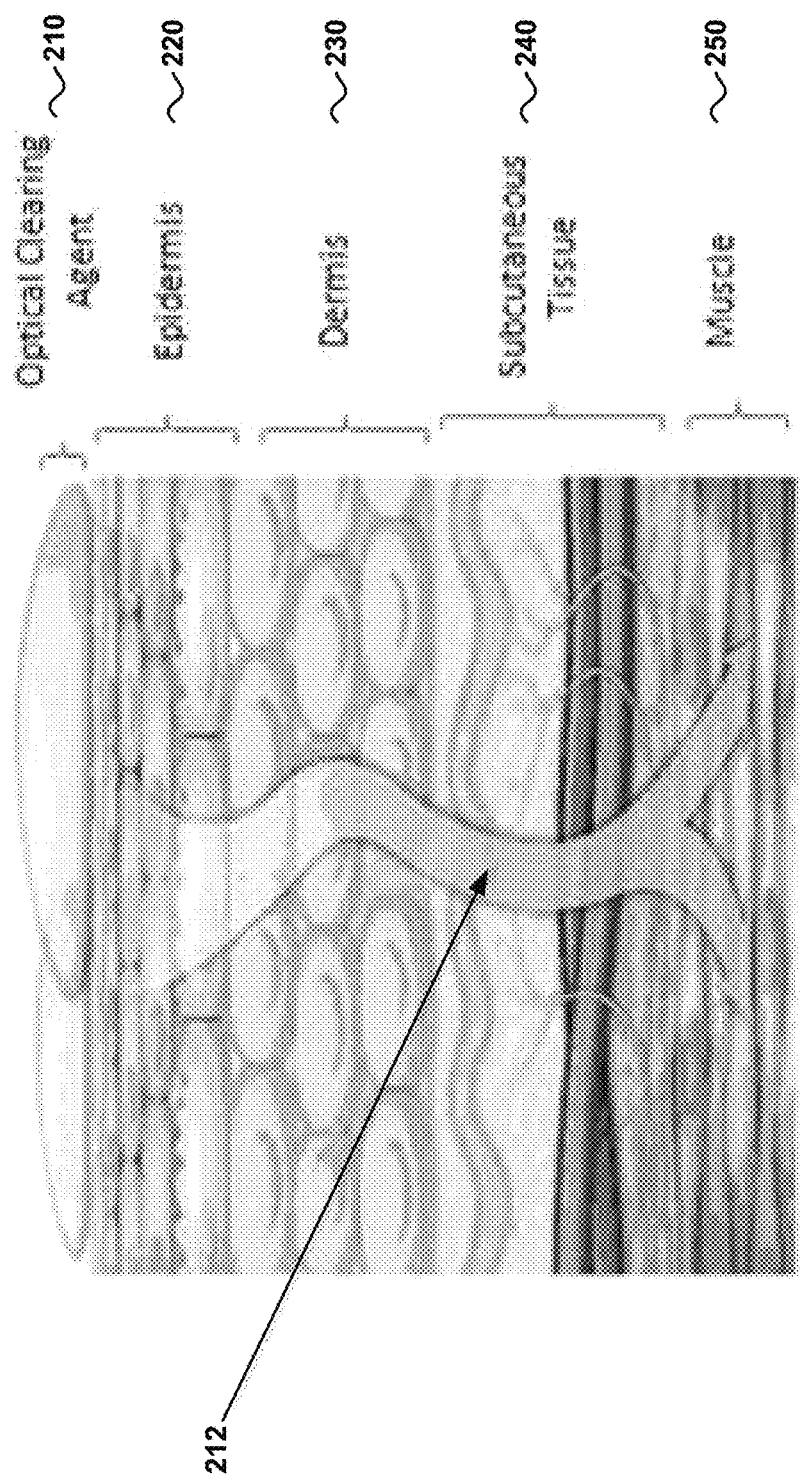
FIG. 2 illustrates the various layers of tissue that a clearing agent can, in various embodiments, penetrate and render more transparent to light.

FIG. 2 illustrates the various layers of tissue that a clearing agent can, in various embodiments, penetrate and render more transparent to light.

Skin is a highly complex tissue, with many inhomogeneities. The principal cell type of the epidermis 220 is the keratinocyte, but it also contains melanocytes and Langerhans cells. The dermis consists mainly of a network of collagen fibers, elastic fibers, and an interfibrillar ground substance consisting of glycosaminoproteoglycans, salts, and water, in addition to fibroblasts, which are the principle cells of the dermis 220.

In an embodiment, a clearing agent 210 is applied to the epidermis 220 of the skin covering a tissue mass, for example, the breast shown in 130 of FIG. 1. The clearing agent can, in various embodiments, penetrate 212 the epidermis 220, the dermis 230, subcutaneous tissue 240 and muscle 250. In penetrating the various layers of tissue 210-250, the clearing agent can render the tissue more transparent to the passage of light, thereby providing for better optoacoustic imaging of such tissue.

In an embodiment, the effectiveness of clearing agent can be enhanced by the use of carrier agents. Carrier agents represent substances that, in an embodiment, when applied to the epidermis 220 of the skin covering a tissue mass, penetrate the epidermis 230 and one or more of the underlying tissue layers 220-250 and facilitate the penetration of clearing agents into such tissue. Carrier agents themselves may, or may not, have skin clearing properties Table 1, immediately below, lists compounds and compositions that can be used as clearing agents and/or carrier agents. The list is intended to be illustrative, and not limiting, and other compounds and compositions now known or later to be developed in the art could be used as clearing agents and/or carrier agents in the methods disclosed herein.

TABLE 1

Clearing Agents and Carrier Agents Useful in Optoacoustic Imaging

| Compounds | Range of the Effective Concentrations (EC), Molecular Weight (MW) and Solubility | Purpose and method of use |
| --- | --- | --- |
| Hyaluronan (Hyaluronic acid) | EC: 0.0001-100%, MW: 5-4,000 kDal, Water Soluble | Carrier agent penetrating skin |
| Chondroitin Sulfate | EC: 0.001-100%, MW: 10-1000 kDal, usually use low MW 5-50 kDa Water Soluble | Carrier agent Penetrating Skin |
| Heparin | EC: 0.001-10%, MW: 5-50 kDa, use 12-16 kDa Water Soluble | Carrier agent Penetrating Skin |
| Keratan Sulfate | EC: 0.001-10%, MW: 5-50 kDa, use 12-16 kDa Water Soluble | Carrier agent Penetrating Skin |
| Acetylsalicylic Acid | EC: 0.001-1% MW 180.16 g/mol completely water and ethanol soluble | Carrier agent Penetrating Skin |
| Urea | EC: 0.001-10%, MW 60.06 g/mol Completely soluble in water (more 100 g/100 ml) | Carrier agent Penetrating Skin and provides partial skin clearance |
| Cyclic Urea | EC: 0.001-10% MW: 128.17 g/mol Soluble in water | Carrier agent Penetrating Skin |
| Dimethyl Sulfoxide | EC: 0.001-10%, MW: 78.13 g/mol Soluble in water; and 100 times less in oil | Carrier agent Penetrating skin |
| TWEEN ® 20 (OR 40 OR 80) Polyoxyethylene (20) sorbitan or Polysorbate | EC: 0.001-1.0% MW: 1228 g/mol Soluble in cold water, methanol, Isopropanol. Polysorbate 20 is dispersible in Cottonseed oil, Ethylene Glycol, and Propylene Glycol; Insoluble in Mineral Oil. | Carrier agent Penetrating Skin |
| Glycerol or 1,2,3-propanetriol; glycerin; glycol alcohol; | EC: 0.1-100% MW: 92.09 g/mol Fully water and ethanol soluble | Carrier agent Penetrating Skin and Optical Clearing Agent for Skin |
| Glucose | EC: 0.1-100% MW: 180.16 g/mol completely water and ethanol soluble | Carrier agent Penetrating Skin and Optical Clearing Agent for Skin |
| Alcohol, ethanol | EC: 0.1-95%, MW: 46.07 g/mol completely water soluble | Carrier agent Penetrating Skin and Optical Clearing Agent for Skin |
| Benzyl alcohol | EC: 0.1-95%, MW: 46.07 g/mol Partially water soluble 4 g/100 ml | Optical Clearing agent for Skin |
| Propylene glycol | EC: 0.001-100% MW: 76.09 g/mol Fully water and ethanol soluble | Optical Clearing agent for skin |
| Polypropylene glycol (PPG) | EC: 0.001-100% MW: 200 to 5000 g/mol, Oil and Water soluble | Optical clearing agent for skin |
| Ethylene glycol | EC: 0.001-100% MW: 62.07 g/mol Fully water and ethanol soluble | Optical clearing agent for skin |
| Polyethylene glycol (PEG) | EC: 0.001-100% MW: 200 to 5000 g/mol, oil and water soluble | Optical clearing agent for skin |

TABLE 1-continued

Clearing Agents and Carrier Agents
Useful in Optoacoustic Imaging

| Compounds | Range of the Effective Concentrations (EC), Molecular Weight (MW) and Solubility | Purpose and method of use |
|---|---|---|
| Polydimethyl-siloxane (dimethicone) | 0.0001-40% MW 6.8-30 kDa Insoluble in water or ethanol; soluble in carbon tetrachloride, diethyl ether, toluene organic solvents | Optical clearing agent for Skin, Used in prior art as component of cosmetic of gels or emulsions |

PEG, PPG and Compositions Thereof as Clearing Agents

Figure 3:
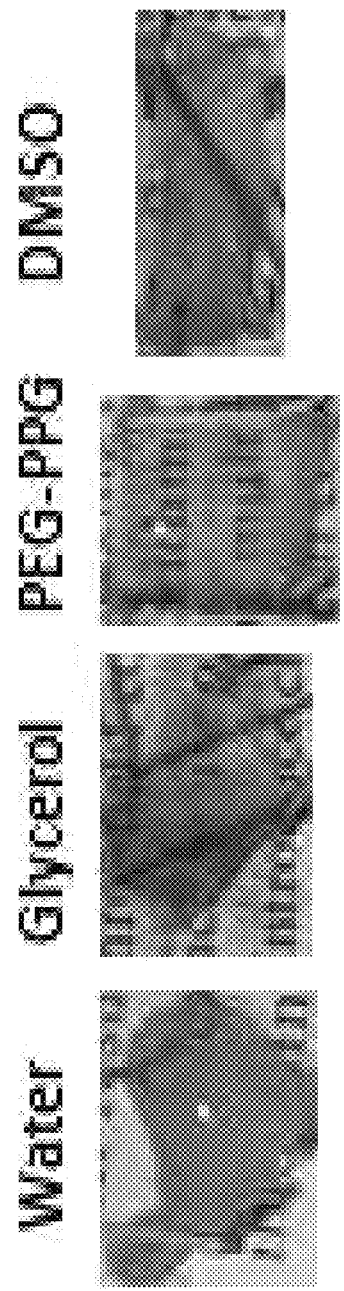
FIG. 3 Illustrates one embodiment of the optical clearing of mouse skin after treatment with potential compounds for coupling gel preparation (40 min).
Figure 4:
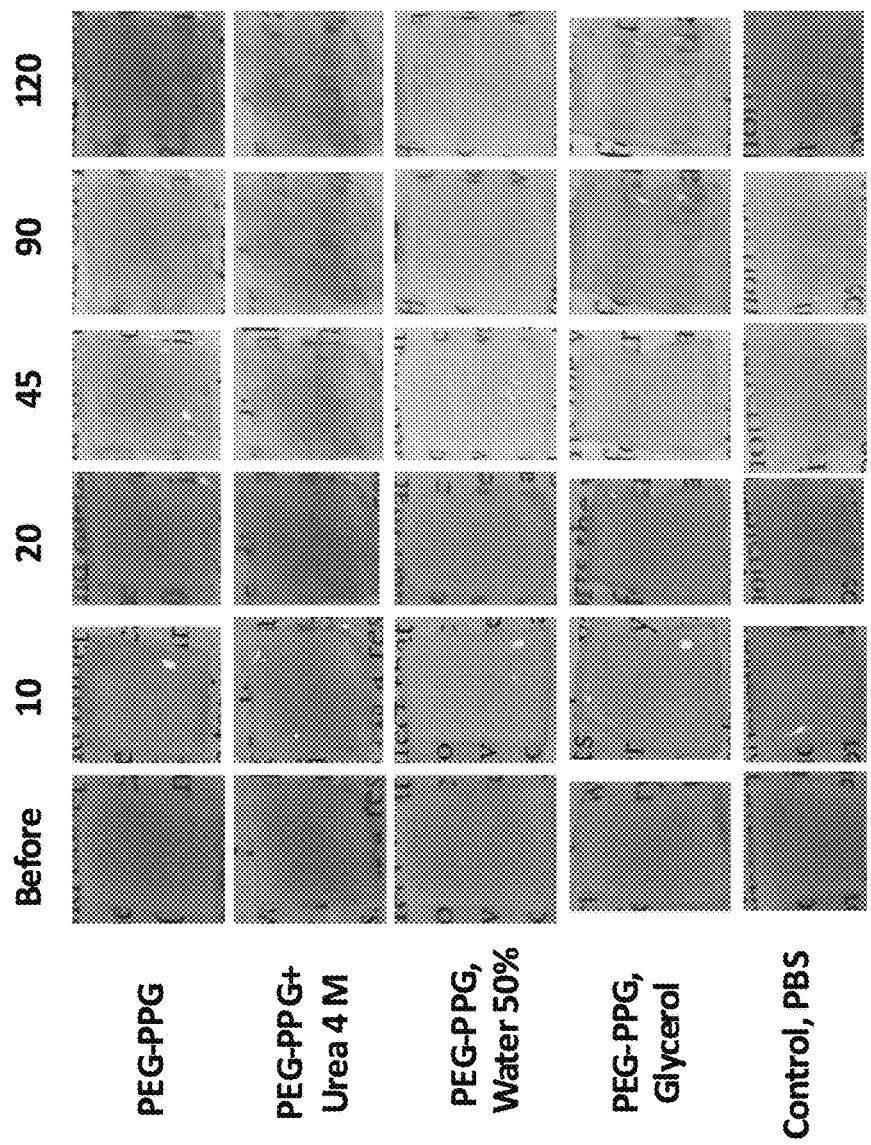
FIG. 4 Illustrates one embodiment of the dynamics of optical clearing of pig skin after treatment of pig skin with different compounds with coupling gel (time expressed in minutes).
Figure 5:
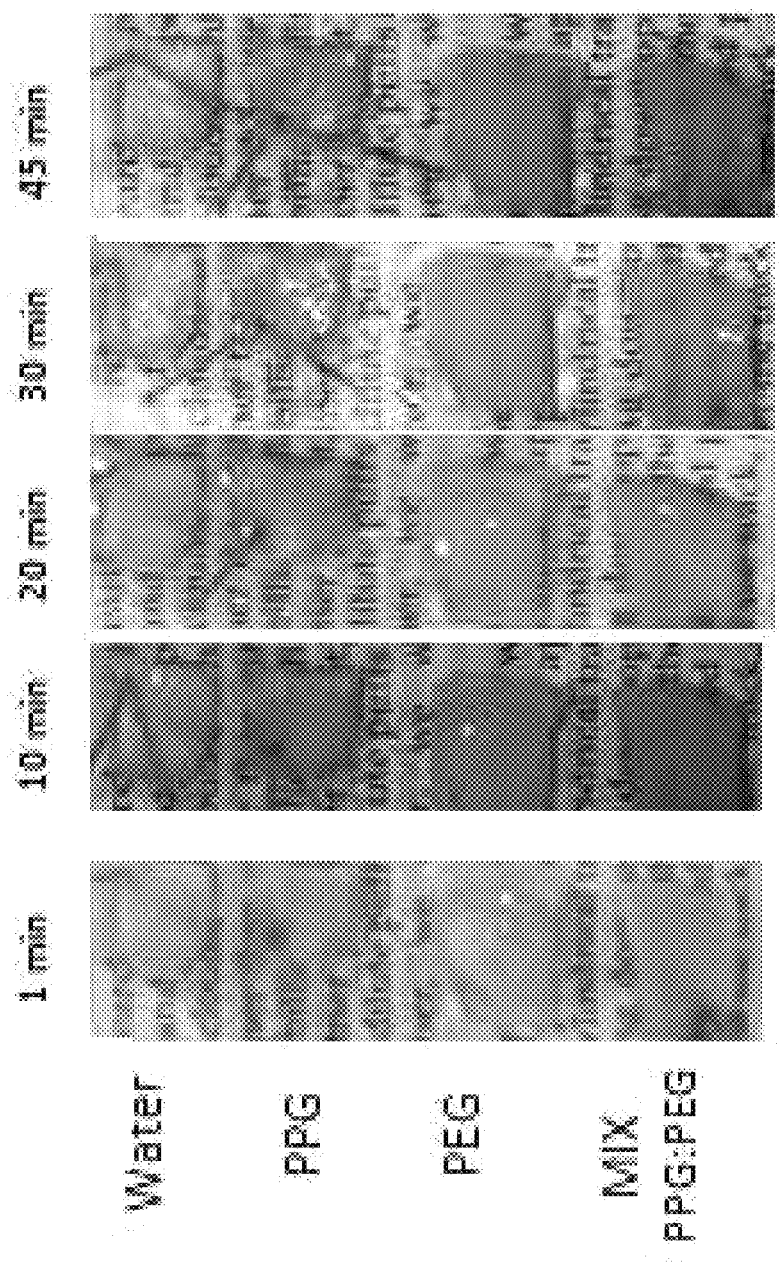
FIG. 5 Illustrates one embodiment of the dynamics of optical clearing after treatment of pig skin with different compounds for coupling gel (time expressed in minutes)

FIGS. 3 to 5 illustrate a sampling of results of tests performed to quantify the effectiveness of PEG, PPG and compositions thereof as clearing agents.

PEG is used in a number of parenteral, intramuscular, and other preparations. On rare occasions, it is used by underground labs to suspend injectable solutions. PEG can be prepared in solution having wide ranging molecular weights (e.g., 200, 300, 400, 500, 600, etc.). Such wide ranging molecular weights are part of what makes PEG such a versatile chemical with numerous applications. For example, it is a solvent in many pharmaceuticals (oral, injectible and topical formulations). PEG is a humectant food addictive (E1520), a moisturizer in medicines, cosmetics, food, toothpaste, and tobacco products, an ingredient in massage oils, carrier in fragrance oils, hand sanitizers, antibacterial lotions, solvent for food colors and flavorings, saline solutions such as eye drops and many other commercial products. The United States Pharmacopeia (USP) approved PEG for use in cosmetics, toiletries, food colorings, cake mixes, salad dressings, soft drinks and more.

Propylene glycol is among the most thoroughly tested and well-understood chemicals. It has been affirmed by the U.S. Food and Drug Administration (FDA) has generally recognized it as safe (GRAS) for use in food for humans and animals (not for cats). It also is approved by the FDA for a variety of uses in drug products. PEG and PPG are chemicals that fall into the broad chemical classification known as "alcohols." Any organic chemical that contains an —OH (oxygen/hydrogen) functional group is an alcohol. The U.S. FDA permits use of the term "alcohol-free" for cosmetics that contain alcohols other than ethanol.

All reagents for the test described below were purchased from Sigma-Aldrich: Urea, U5378 for molecular biology (powder), Propylene glycol W294004, Polypropylene glycol (PPG) 202304 average Mn 425, Polyethylene glycol (PEG) 202398—average Mn 400, Polyethylene glycol-ran-propylene glycol 438197—Mn~2,500, Dimethyl sulfoxide (DMSO) D8418, Glycerol G5516—for molecular biology, ≥99%.

The skin of nude mice and young pig was harvested, and the underlying muscle layer was removed with precision. The freshly prepared skin (thickness for mice of 0.85±0.08 mm, for pig of 1.45±0.25) was placed over a resolution target and exposed to clearing agents for different periods of time. Photographs were taken with a high resolution digital camera. Optical property measurements were performed on in vitro samples of young pig skin. Spectrophotometer measurements were made with an Oceanoptics USB4000 with Micropack Halogen Light Source HL-2000 FHSA spectrophotometer capable of scanning wavelengths of 500-1400 nm for calculating the amount of light transmission through the pig skin.

For the first part of experiments, mouse skin was utilized. Native skin samples, which had not been treated with any chemical agents, were used as controls, but were treated with water or physiological saline. Treatment with glycerol, PPG-PEG mixture and DMSO are presented in FIG. 3. The agents were applied to the dermal side of the skin samples for periods of 40 min. As is readily apparent, the optical clearing of mouse skin after treatment was significantly better for the glycerol, and the PPG and PEG mixture.

In another set of experiments, experiments, the dynamics of the clearing effect of various clearing agent compounds and compositions was tested on pig skin. FIG. 4 shows how the degree of clearing of pig for various mixtures varies over time. In this experiment, a mixture of PPG-PEG and glycerol proved most effective, with maximum clearing effect occurring in 90 to 120 minutes.

In another set of experiments, the dynamics of the clearing effect PEG, PPG and mixtures thereof, was texted on pig skin. FIG. 5 shows how the degree of clearing of pig skin by PEG, PPG and mixtures thereof, varies over time. In this experiment, a mixture of PPG-PEG proved most effective, with maximum clearing effect occurring in 30 to 45 minutes.

Figure 6:
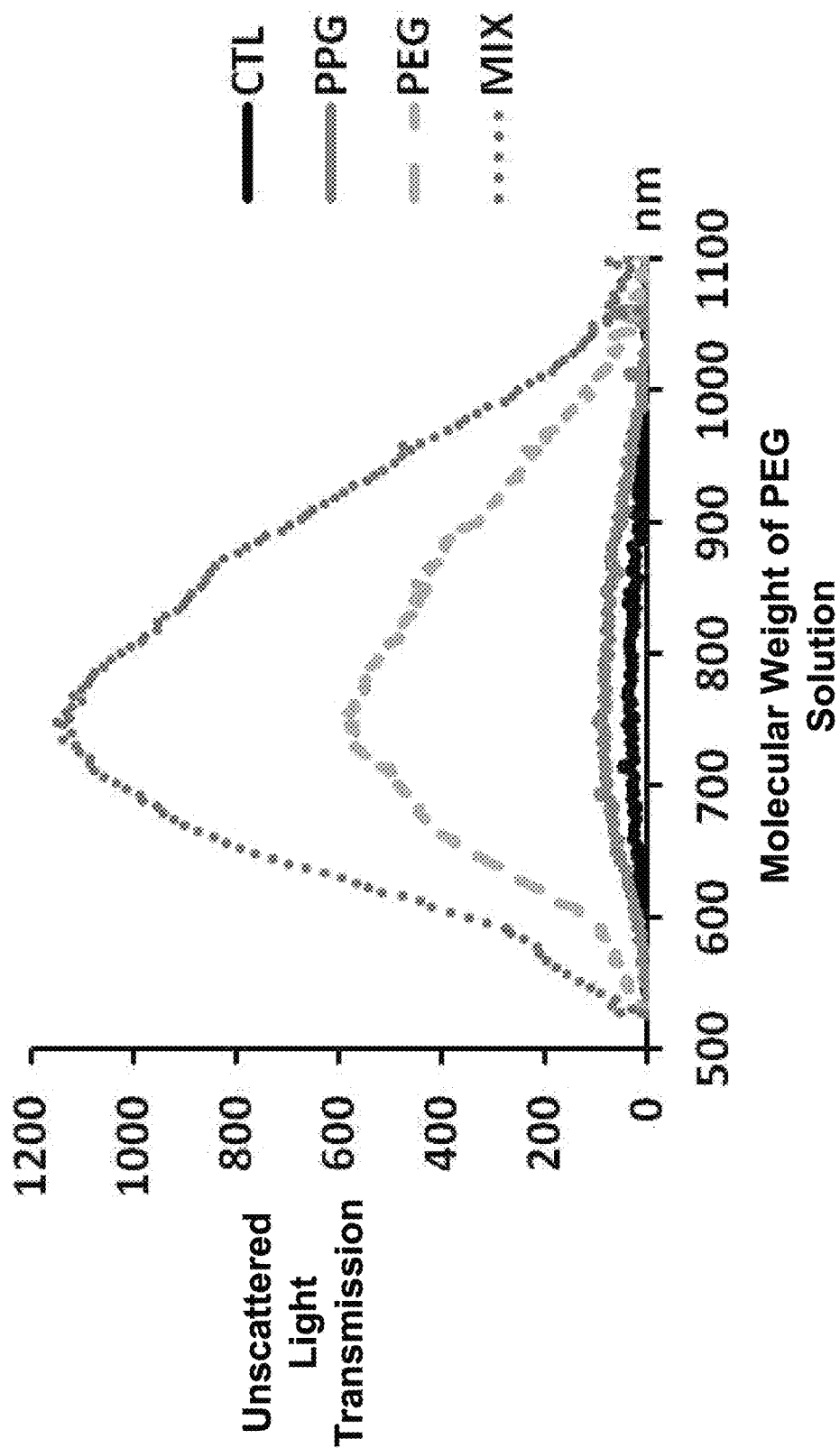
FIG. 6 illustrates one embodiment of unscattered transmission (after treatment 60 min with PPG, PEG and their mixture).

In another set of experiments, the unscattered transmission of light by pig skin was tested 60 minutes after treatment with PPG, PEG and their mixture using various molecular weights of PEG. FIG. 6 graphically illustrates the results of these experiments. The results suggest that a mixture of PPG and PEG is generally more effective as a clearing agent than either alone, and that mixtures utilizing PEG of a molecular weight between 700 and 800 are most effective.

Short-term goals will focus on investigating applications of PPG and PEG-based combinations with additional moisturization of skin using natural agents such as, for example, Glycosaminoglycans or mucopolysaccharides to prevent of dehydration and support gel delivery into the skin.

Utilizing Hyaluronic Acid as a Carrier Agent

Figure 7:
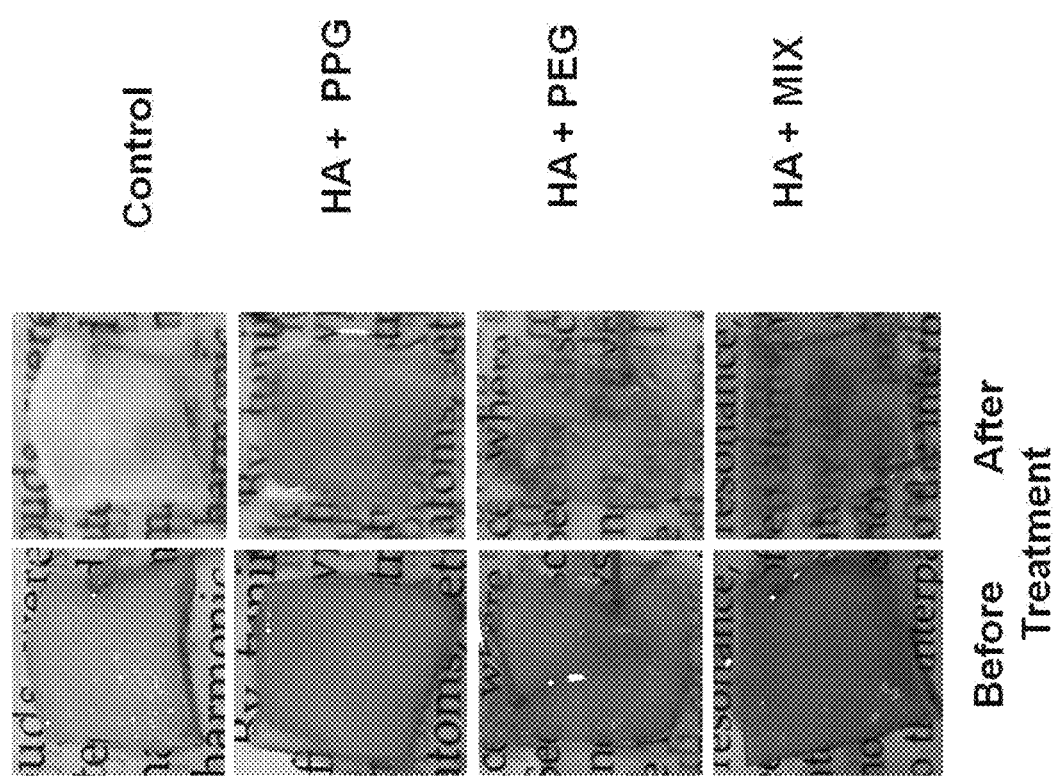
FIG. 7 Illustrates one embodiment of optical clearing of pig skin after pretreatment with hyaluronic acid (30 min) of pig skin and treatment with different compounds for coupling gel (45 min).
Figure 8:
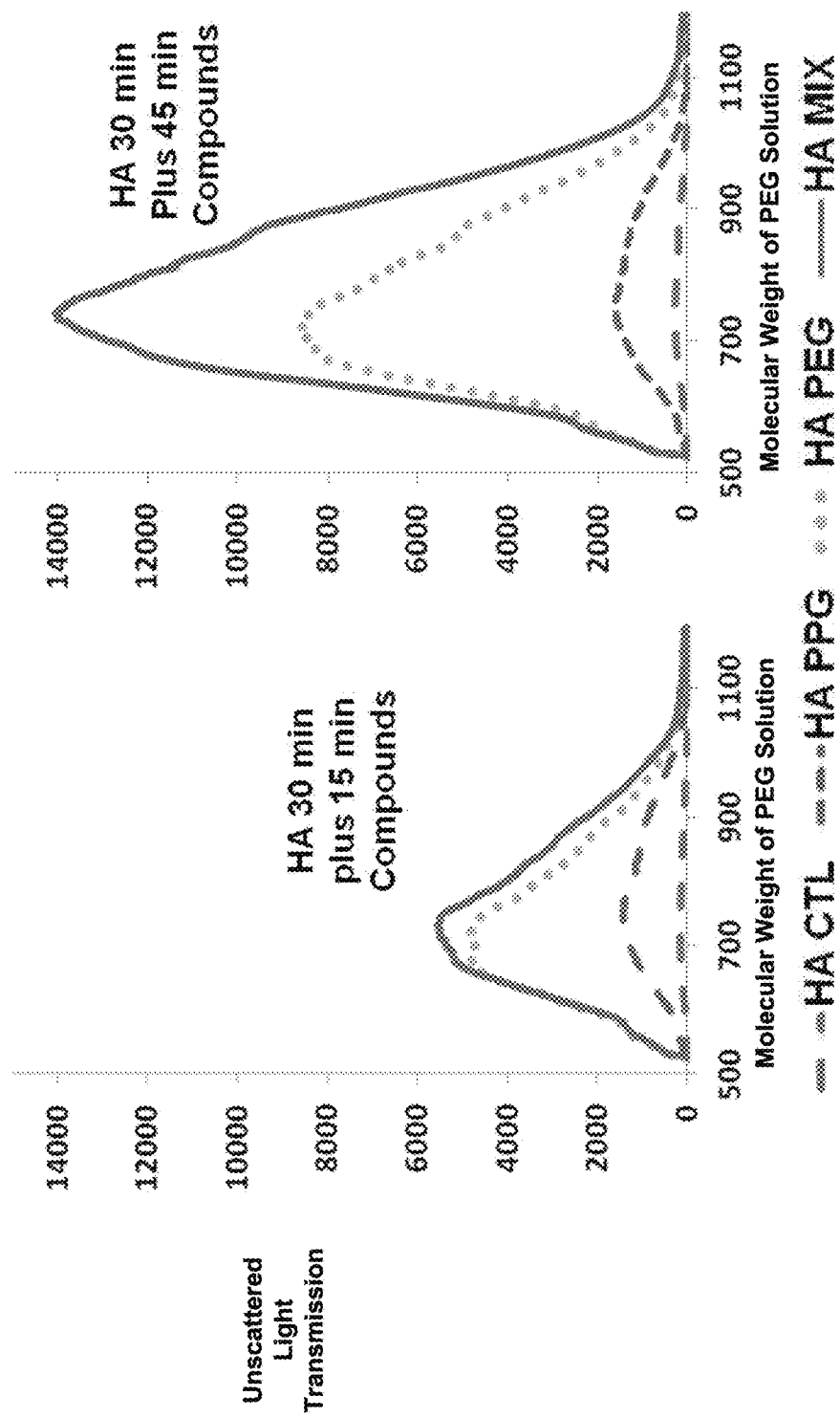
FIG. 8 Illustrates one embodiment of unscattered transmission of pig skin after pretreatment with hyaluronic acid and treatment with PPG, PEG and their mixture after 15 and 45 minutes.
Figure 9:
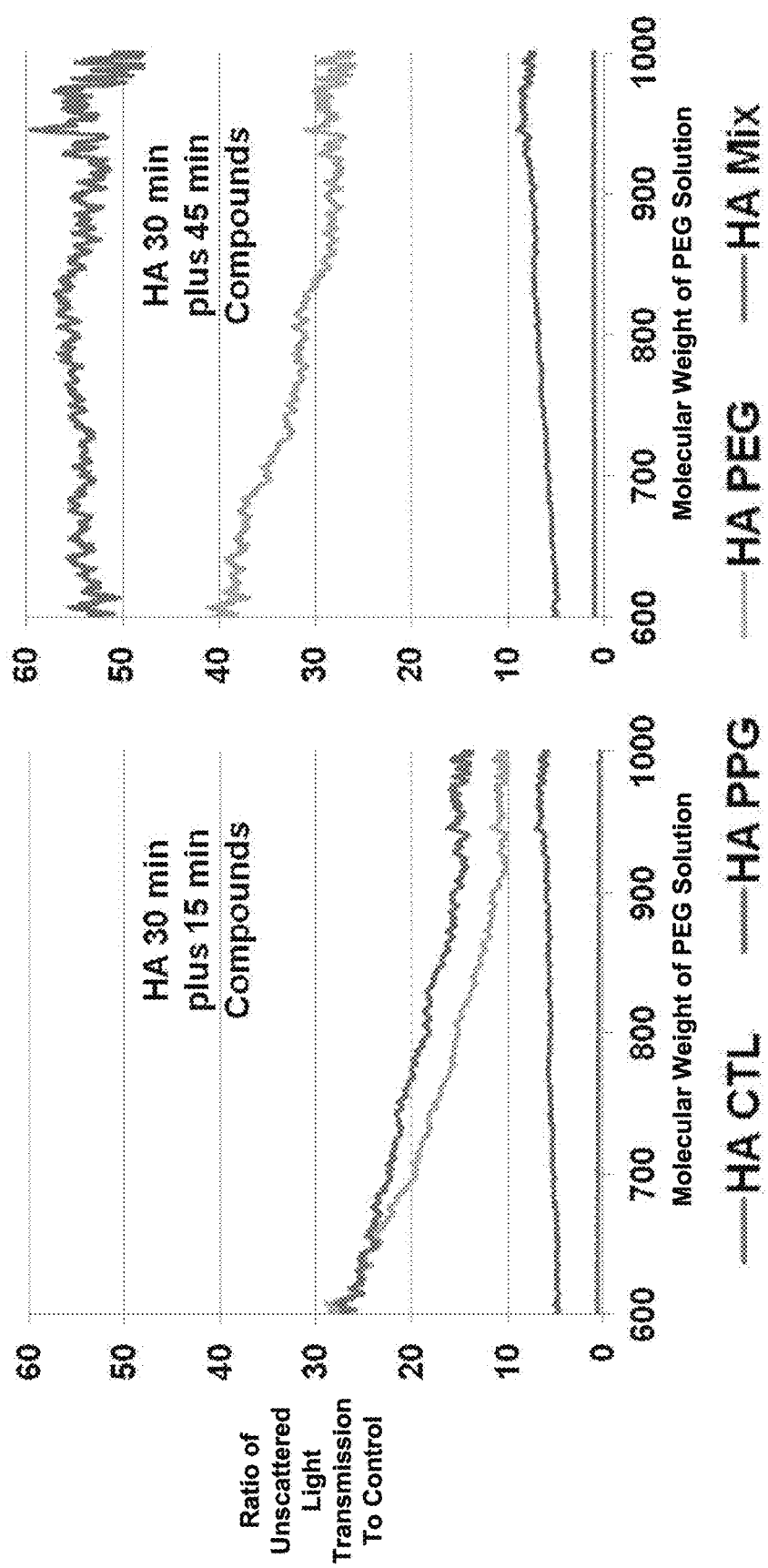
FIG. 9 Illustrates one embodiment of the ratio of unscattered transmission in pig skin after pretreatment with hyaluronic acid and treatment with PPG, PEG and their mixture after 15 and 45 min normalized to control skin pretreated with hyaluronic acid only.

The effectiveness of various compounds and compositions as carriers for optoacoustic clearing agents, such as PPG, PEG and mixtures thereof was tested using a number of different potential carriers such as, for example, the compounds listed in Table 1 above as carrier agents. FIGS. 7 to 9 illustrate exemplary tests utilizing hyaluronic acid (hyaluronic acid) as a carrier for PPG, PEG and mixtures thereof.

Hyaluronic acid is a naturally occurring biopolymer, which serves important biological functions in bacteria and higher animals including humans. It is found in most connective tissues and is particularly concentrated in synovial fluid, the vitreous fluid of the eye, umbilical cords and chicken combs. Hyaluronan or Hyaluronic acid is a non-sulphated, straight-chain glycosaminoglycan polymer of the extracellular matrix.

Half of total-body hyaluronic acid is located within skin, and is responsible for skin hydration. Hyaluronic acid has a complex metabolically rate with rapid turnover in skin. There are wide differences occurring in dermal and epidermal compartments. Hyaluronic acid (hyaluronic acid) is a carbohydrate, more specifically a mucopolysaccharide, occurring naturally in all living organisms. It can be several thousands of sugars (carbohydrates) long (Necas et all 2008). The polysaccharide hyaluronic acid is a linear polyanion, with a poly repeating disaccharide structure: [(1→3)-β-d-GlcNAc-(1→4)-β-d-GlcA-].

The uronic acid and aminosugar in the disaccharide are D-glucuronic acid and d-N-acetyl-glucosamine, and are linked together through alternating beta-1,4 and beta-1,3 glycosidic bonds (see Chemical structure, Scheme 1).

Scheme 1. Chemical Structure of Hyaluronic Acid

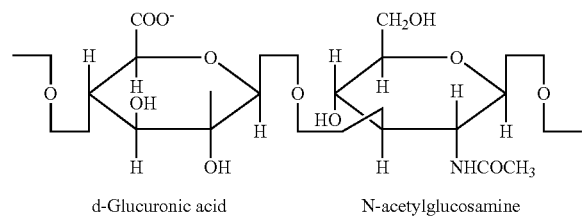

d-Glucuronic acid        N-acetylglucosamine

The term "hyaluronic acid" (HA) is in fact usually used as meaning a whole series of polysaccharides with alternating residues of D-glucuronic and N-acetyl-D-glucosamine acids with varying molecular weights or even the degraded fractions of the same, and it would therefore seem more correct to use the plural term of "hyaluronic acids".

Hyaluronan, HA is member of the glycosaminoglycan family vary in the type of hexosamine, hexose or hexuronic acid unit they contain glucuronic and iduronic acid, galactose, galactosamine, glucosamine and others. One skilled in the art can name several examples of glycosaminoglycans:

Chondroitin sulfate is a sulfated glycosaminoglycan (GAG) composed of a chain of alternating sugars. It is usually found attached to proteins as part of a proteoglycans.

Dermatan sulfate is a GAG too, but formerly called a mucopolysaccharide.

Keratan sulfate (keratosulfate), is sulfated glycosaminoglycans (structural carbohydrates) that have been found especially in the cornea, cartilage, central nervous system and bone.

Heparin and very closely Heparan sulfate, is a members of the glycosaminoglycan family of carbohydrates.

Hyaluronic acid is one of the most hydrophilic (water-loving) molecules in nature and has been described as nature's moisturizer. As mentioned, the polymer in solution assumes a stiffened helical configuration, which can be attributed to hydrogen bonding between the hydroxyl groups along the chain. As a result, a coil structure is formed that traps approximately 1 000 times its weight in water.

Various studies have demonstrated that hyaluronan is highly non-antigenic and non-immunogenic, owing to its high structural homology across species, and poor interaction with blood components and is generally not cytotoxic. The effects of HA on skin do not depend on the nature of the sources of this compound. The viscoelastic nature of hyaluronic acid along with its biocompatibility and non-immunogenicity has led to its use in a variety of clinical applications.

In the tests illustrated in FIGS. 7 to 9, freshly prepared pig skin (thickness of 1.5±0.2 mm) was placed over a resolution target and exposed to hyaluronic acid, followed by various clearing agents for different periods of time. Photographs were taken with a high resolution digital camera. Optical property measurements were performed on in vitro samples of young pig skin. Spectrophotometer measurements were made with an Oceanoptics USB4000 spectrophotometer with Micropack Halogen HL-2000FHSA light source capable of scanning wavelengths of 500-1400 nm for collecting the amount of light transmission through the pig skin.

Native skin samples were used as controls after pretreatment with hyaluronic acid and water or PBS The agents were applied to the dermal side of the skin samples for periods of 30 min for hyaluronic acid pretreatment, and followed by dynamic applications from 5 to 45 minutes) for PPG, PEG and mixtures thereof.

FIG. 7 shows the optical clearing of pig skin after pretreatment with hyaluronic acid (30 minutes) followed by application of PPG, PEG and a mixture thereof (45 minutes). Pretreatment with hyaluronic acid provides greater transparency of the skin (contrast, for example, FIG. 5) and a mixture using PPG and PEG yields the greatest transparency.

FIG. 8 graphically illustrates the unscattered transmission of pig skin after pretreatment with hyaluronic acid and treatment with PPG, PEG and their mixture after 15 and 45 minutes. The results generally show that hyaluronic acid alone has minimal clearing effects, but that it enhances the clearing effect of PEG and mixtures of PPG and PEG (contrast, for example, FIG. 6) and that mixtures having PEG solutions at a molecular weight of 700 to 800 are most effective in increasing skin transparency. The level of unscattered transmission after pretreatment with hyaluronic acid and treatment with MIX of PPG-PEG is more than 50 times better as compared to the hyaluronic acid control samples.

FIG. 9 graphically illustrates the ratio of unscattered transmission in pig skin after pretreatment with hyaluronic acid and treatment with PPG, PEG and their mixture after 15 and 45 min normalized to control skin. The results generally show significantly increased skin transparency after pretreatment with hyaluronic acid and treatment with PEG or a mixture of PPG and PEG, the latter being the most effective.

These experiments show that the pretreatment of skin with hyaluronic acid combined with the application of the PPG- and PEG-based polymer mixture greatly facilitates light penetration through intact skin, and can reduce dermal scattering and significantly enhance optical clearing.

Figure 10:
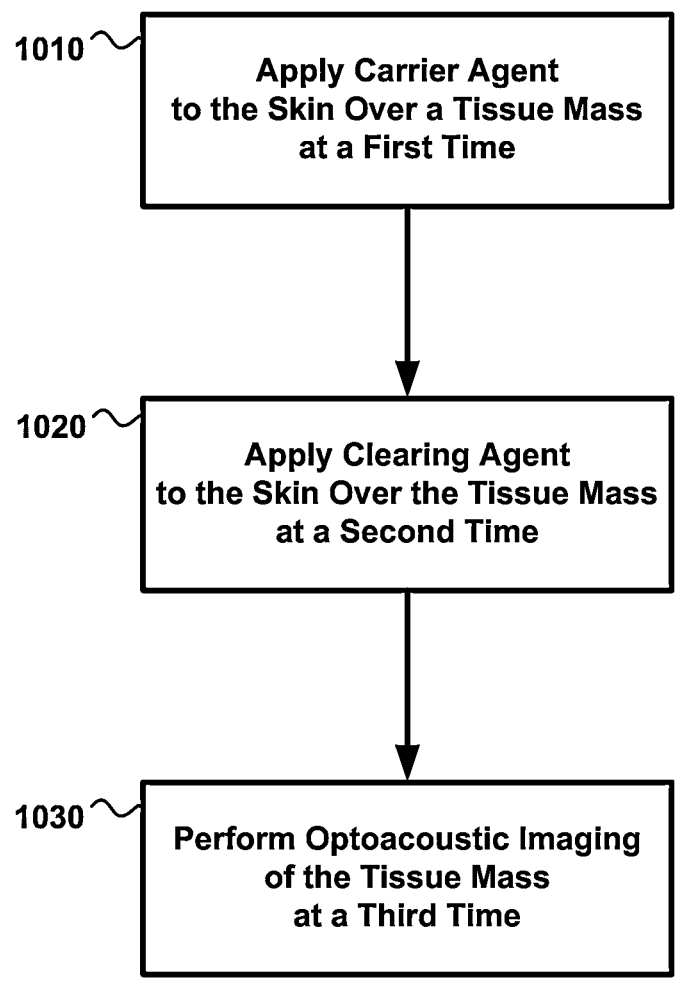
FIG. 10 is a flow chart illustrating an embodiment of a method for the use of carrier agents and clearing agents in optoacoustic imaging.

An Exemplary Methodology for the Use of Carrier Agents and Clearing Agents in Optoacoustic Imaging FIG. 10 is a flow chart illustrating an embodiment of a method for the use of carrier agents and clearing agents in optoacoustic imaging.

In block 1010 of the method, a cattier agent is applied, at a first time, to the skin overlying a tissue mass that is to be imaged using optoacoustic imaging techniques at a first time. In an embodiment, the carrier agent is any compound or composition now known, or later to be developed in the art, that is capable of acting as a carrier agent for a clearing agent. In an embodiment, the carrier agent is any of the compounds listed in Table 1 as a carrier agent. In an embodiment, the carrier agent is any of the compounds listed in Table 1 as a carrier agent used in the concentrations indicated in Table 1. In an embodiment, the carrier agent is a composition comprising a mixture of one or more of the compounds listed in Table 1 as a carrier agent. In an embodiment, the absorption a carrier agent into the skin is enhanced by one or more of warming the skin prior to application, applying carrier agent using a patch to avoid evaporation and/or applying a pin-array to the skin to partially distort the stratum corneum of the skin.

In an embodiment, the carrier agent is hyaluronic acid. One skilled in the art can distinguish three types of hyaluronic acid based on their average molecular weight: 5,000-100,000 Da, 200,000-400,000 Da and 400,000-1,000, 000 Da. In an embodiment, carrier agents using hyaluronic acid of about 50,000 Dalton are used.

In an embodiment, the carrier agent comprises high viscosity hyaluronic acid biopolymers having molecular weight from about $5 \times 10^3$ to maximum weight of about $4 \times 10^6$ Dalton. Such carrier agents can provide moisturizing of skin by endogenous water and without significant penetration of hyaluronic acid itself into the skin.

In the application of the carrier to the skin is formulated to deliver at least two hyaluronic acid fractions or salts thereof, wherein the first fraction has an average molecular weight in the range of 8,000-100,000 Da, 10-90 kDa, 30-70 kDa, or about 50 kDa; and the second fraction has an average molecular weight in the range of 500,000-1,000,000 Da, 600-900 kDa, 700-800 kDa, or around 750 kDa.

In an embodiment, the carrier agent is 25-50% DMSO in water. In an embodiment, the carrier agent is 50% Urea diluted in water.

In block 1020 of the method, a clearing agent is applied, at a second time, to the skin overlying the tissue mass. In an embodiment, the time difference between the first time and the second time is any time difference adequate to enable the carrier agent to enhance the penetration of a clearing agent into the skin. In an embodiment, the time difference between the first time and the second time is about 30 minutes. In an embodiment, the time difference between the first time and the second time is about 45 minutes. In an embodiment, the time difference between the first time and the second time is between 30 to 90 minutes.

In an embodiment, the clearing agent is any compound or composition now known, or later to be developed in the art, that is capable of acting as a clearing agent. In an embodiment, the clearing agent is any of the compounds listed in Table 1 as a clearing agent. In an embodiment, the clearing agent is any of the compounds listed in Table 1 as a clearing agent used in the concentrations indicated in Table 1. In an embodiment, the clearing agent is a composition comprising a mixture of one or more of the compounds listed in Table 1 as a clearing agent. In an embodiment, the clearing agent is PPG in a concentration of about 425 g/mol. In an embodiment, the clearing agent is PEG in a concentration of about 420 g/mol. In an embodiment, the clearing agent is a composition of low molecular weight (PEG+PPG) in equal parts (50/50). In an embodiment, PEG and PPG can be diluted in water, up to about two times.

In block 1030 of the method, the tissue mass is imaged using optoacoustic imaging techniques at a third time. In an embodiment, the time difference between the second time and the third time is any time difference adequate to enable the clearing agent to have a clearing effect on the skin. In an embodiment, the time difference between the second time and the third time is about 30 minutes. In an embodiment, the time difference between the second time and the third time is about 45 minutes. In an embodiment, the time difference between the second time and the third time is between 30 to 90 minutes.

In an embodiment, prior to optoacoustic imaging, optically and acoustically transparent gel (e.g. low viscosity clear Parker AquaSonic gel) is applied to the skin over the tissue mass as a coupling agent. In an embodiment, coupling agents used during optoacoustic imaging can additionally or alternatively comprise carrier agents or clearing agents such as, for example, those listed in Table 1 above.

CONCLUSION

Those skilled in the art will recognize that the methods and systems of the present disclosure may be implemented in many manners and as such are not to be limited by the foregoing exemplary embodiments and examples. In other words, functional elements being performed by single or multiple components, in various combinations of hardware and software or firmware, and individual functions, may be distributed among software applications at either the client level or server level or both. In this regard, any number of the features of the different embodiments described herein may be combined into single or multiple embodiments, and alternate embodiments having fewer than, or more than, all of the features described herein are possible. Functionality may also be, in whole or in part, distributed among multiple components, in manners now known or to become known. Thus, myriad software/hardware/firmware combinations are possible in achieving the functions, features, interfaces and preferences described herein. Moreover, the scope of the present disclosure covers conventionally known manners for carrying out the described features and functions and interfaces, as well as those variations and modifications that may be made to the hardware or software or firmware components described herein as would be understood by those skilled in the art now and hereafter.

Furthermore, the embodiments of methods presented and described as flowcharts in this disclosure are provided by way of example in order to provide a more complete understanding of the technology. The disclosed methods are not limited to the operations and logical flow presented herein. Alternative embodiments are contemplated in which the order of the various operations is altered and in which sub-operations described as being part of a larger operation are performed independently.

While various embodiments have been described for purposes of this disclosure, such embodiments should not be deemed to limit the teaching of this disclosure to those embodiments. Various changes and modifications may be made to the elements and operations described above to obtain a result that remains within the scope of the systems and processes described in this disclosure.

We claim:
1. A two-stage method for optoacoustic imaging of tissue in vivo, the method comprising the steps of:
topically applying a penetration-facilitating carrier agent comprising hyaluronic acid or a hyaluronic acid salt to skin overlying a surface of at least a portion of the tissue;
after a time period of 30 to 90 minutes has elapsed after the topically applying the penetration-facilitating carrier agent, such that the penetration-facilitating carrier agent has penetrated the epidermis of the skin, topically applying a clearing agent comprising a mixture of polyethylene glycol and polypropylene glycol to the skin overlying the surface of the at least a portion of the tissue, wherein the penetration-facilitating carrier facilitates penetration of the clearing agent into the tissue and the clearing agent renders the skin more transparent to light relative to when no clearing agent is applied;
imaging the tissue using optoacoustic imaging techniques, the optoacoustic imaging techniques comprising the steps of:
irradiating the tissue with a laser pulse, causing heating and expansion of the tissue;
receiving ultrasound using an array of ultrasonic transducers;
analyzing information received by the array of ultrasonic transducers during a period following the laser pulse; and,
constructing an image.

2. The method of claim 1 wherein the imaging comprises acoustically coupling an optoacoustic probe to the tissue using an optically and acoustically transparent gel as a coupling agent.

3. The method of claim 1, wherein the hyaluronic acid or hyaluronic acid salt has a molecular weight in the range from 5000 Dalton to 100,000 Dalton.

4. The method of claim 1, wherein the hyaluronic acid or hyaluronic acid salt have molecular weight in the range from 200,000 Dalton to 400,000 Dalton.

5. The method of claim 1, wherein the hyaluronic acid or hyaluronic acid salt have molecular weight in the range from 400,000 Dalton to 1,000,000 Dalton.

6. The method of claim 1, wherein the mixture comprises equal parts of polyethylene glycol and polypropylene glycol.

7. The method of claim 1, wherein optically and acoustically transparent gel is applied to the skin overlying the at least a portion of the tissue during the imaging after the step of applying a clearing agent, and wherein said gel may contain PEG and PPG.

8. A method for optoacoustic imaging of a tissue mass in vivo, the method comprising:
   topically applying a penetration-facilitating carrier agent to skin overlying at least a portion of the tissue mass, the penetration-facilitating carrier agent comprising hyaluronic acid;
   after a time period sufficient to enable the penetration-facilitating carrier agent to penetrate the epidermis of the skin has elapsed after the topically applying of the penetration-facilitating carrier agent, topically applying a clearing agent to the skin overlying the at least a portion of the tissue mass, the clearing agent comprising a mixture of polyethylene glycol and polypropylene glycol, wherein the penetration-facilitating carrier facilitates penetration of the clearing agent into the skin overlying the at least a portion of the tissue mass and the clearing agent renders the skin more transparent to light relative to when no clearing agent is applied; and
   imaging the tissue mass using optoacoustic imaging techniques, the optoacoustic imaging techniques comprising the steps of:
      irradiating the tissue mass with a laser pulse, causing heating and expansion of the tissue mass;
      receiving ultrasound using an array of ultrasonic transducers;
      analyzing information received by the array of ultrasonic transducers during a period following the laser pulse; and,
      forming an image.

9. The method of claim 8, wherein the time period sufficient to enable the penetration-facilitating carrier agent to penetrate the epidermis of the skin is from 30 minutes to 90 minutes.

10. A method for optoacoustic imaging of a tissue in vivo, the method comprising:
   topically applying a penetration-facilitating carrier agent to skin overlying a surface of at least a portion of the tissue at a first time;
   topically applying a clearing agent to the skin overlying the surface of at least a portion of the tissue at a second time, the second time being a time later than the first time; and
   imaging the tissue using optoacoustic imaging at a third time, the third time being a time later than the second time,
   wherein the penetration-facilitating carrier facilitates penetration of the clearing agent into the tissue and the clearing agent renders the skin more transparent to light relative to when no clearing agent is applied.

11. The method of claim 10, wherein the penetration-facilitating carrier agent is selected from the group consisting of hyaluronic acid, salts of hyaluronic acid, chondroitin sulfate, heparin, keratan sulfate, acetylsalicylic acid, urea, cyclic urea, dimethyl sulfoxide, polysorbate 20, polysorbate 40, polysorbate 80, glycerol, and combinations thereof.

12. The method of claim 10, wherein the penetration-facilitating carrier agent is hyaluronic acid or a salt of hyaluronic acid.

13. The method of claim 10, wherein the clearing agent is selected from the group consisting of glycerol, 1,2,3-propanetriol, glycerin, glycol alcohol, glucose, ethanol, benzyl alcohol, propylene glycol, polypropylene glycol, ethylene glycol, polyethylene glycol, polydimethylsiloxane, and combinations thereof.

14. The method of claim 10, wherein the clearing agent is a mixture of polyethylene glycol and polypropylene glycol.

15. The method of claim 10, wherein the time difference between the first time and the second time is from 30 minutes to 90 minutes.

16. The method of claim 10, wherein the time difference between the second time and the third time is from 30 minutes to 90 minutes.

* * * * *